United States Patent [19]

Ferenz

[11] Patent Number: 5,681,939
[45] Date of Patent: Oct. 28, 1997

[54] DIRECT ESTERIFICATION OF PROPOXYLATED GLYCERIN

[75] Inventor: Michael R. Ferenz, Coatesville, Pa.

[73] Assignee: ARCO Chemical Technology, L.P., Greenville, Del.

[21] Appl. No.: 518,088

[22] Filed: Aug. 22, 1995

[51] Int. Cl.$^6$ .................... A21D 2/16; A23D 9/013; C07H 13/06; C07H 1/00
[52] U.S. Cl. .......................... 536/18.6; 554/124
[58] Field of Search .................. 554/149, 148, 554/124; 536/18.6

[56] References Cited

U.S. PATENT DOCUMENTS

| | | | |
|---|---|---|---|
| 3,337,595 | 8/1967 | Lament | 260/410.6 |
| 4,614,622 | 9/1986 | Huettinger et al. | 260/410.7 |
| 4,849,242 | 7/1989 | Kershner | 426/601 |
| 4,861,613 | 8/1989 | White et al. | 426/611 |
| 4,983,329 | 1/1991 | Cooper | 260/410.7 |
| 5,059,443 | 10/1991 | Ennis et al. | 426/531 |
| 5,077,073 | 12/1991 | Ennis et al. | 426/531 |
| 5,118,448 | 6/1992 | Cooper | 554/168 |
| 5,304,665 | 4/1994 | Cooper et al. | 554/149 |
| 5,308,634 | 5/1994 | Cooper | 426/531 |
| 5,371,253 | 12/1994 | Cooper | 554/173 |
| 5,399,729 | 3/1995 | Cooper et al. | 554/149 |
| 5,466,843 | 11/1995 | Cooper | 554/149 |

FOREIGN PATENT DOCUMENTS

| | | |
|---|---|---|
| 0481523A1 | 4/1992 | European Pat. Off. |
| 207070 | 2/1984 | Germany |
| 55-79313 | 6/1980 | Japan |

Primary Examiner—Gary L. Kunz
Attorney, Agent, or Firm—Stephen D. Harper

[57] ABSTRACT

Propoxylated glycerin is esterified with excess fatty acid by a process wherein the temperature is increased incrementally and the pressure is reduced incrementally during the course of esterification while removing the water formed as a by-product. Rapid conversion of the hydroxyl groups of the propoxylated glycerin is achieved while minimizing losses of fatty acid. The fatty acid-esterified propoxylated glycerin obtained thereby is useful as a reduced calorie fat substitute.

15 Claims, No Drawings

DIRECT ESTERIFICATION OF PROPOXYLATED GLYCERIN

FIELD OF THE INVENTION

This invention relates to methods for esterifying a propoxylated glycerin using an excess of fatty acid. In particular, the invention pertains to an improved esterification process wherein losses of fatty acid are minimized while accomplishing rapid conversion of the hydroxyl groups of the propoxylated glycerin.

BACKGROUND OF THE INVENTION

Fatty acid-esterified propoxylated glycerins have been proposed for use as reduced calorie fat substitutes in food products, as disclosed in U.S. Pat. No. 4,861,613 (White et al.). A number of different methods of synthesizing useful food ingredients of this type have been described. U.S. Pat. No. 4,983,329 (Cooper), for example, teaches that esterified propoxylated glycerin may be obtained by reacting a propoxylated glycerin with excess $C_{10}$–$C_{24}$ fatty acids at temperatures of from about 100° C. to about 250° C. The patent additionally suggests that the esterification rate can be enhanced by carrying out the reaction under reduced pressures of from about 0.01 mm up to atmospheric with gas or low boiling liquid stripping. One of the problems associated with such an esterification process is that unreacted fatty acid tends to be removed from the reaction zone during esterification. The fatty acid is taken overhead not only as a consequence of the low pressures and high temperatures encountered during esterification, but also because of the tendency of the fatty acid to steam distill together with the water generated by the esterification reaction. Since it will generally be desirable to accomplish a high degree of conversion of the hydroxyl groups of the propoxylated glycerin starting material (generally, at least 90%) and to do so in the absence of any catalyst (other than excess fatty acid) in view of the difficulties and cost associated with removing such substances quantitatively from food grade products, such losses of unreacted fatty acid will generally result in off-specification product (e.g., insufficiently esterified propoxylated glycerin) or uneconomically long batch times. The aforementioned patent indicates that any fatty acid removed overhead may be recycled back to the reaction zone. While such recycling may be feasible, it is not desirable from a commercial point of view since special equipment and facilities would be needed which would add to the overall cost of producing an esterified propoxylated glycerin. Moreover, certain fatty acids such as long chain saturated fatty acids are difficult to recycle due to their relatively high melting points and their tendency to foul processing equipment when taken overhead. It would consequently be highly advantageous to develop a rapid direct esterification method whereby the need to recycle fatty acid is avoided.

SUMMARY OF THE INVENTION

The invention provides a process for producing a fatty acid-esterified propoxylated glycerin comprising the following steps. A reaction mixture comprised of a propoxylated glycerin and a molar excess of fatty acid is formed in a reaction zone at an initial temperature of from about 20° C. to 80° C. and an initial pressure of from about 13 to 16 psia. Simultaneously, the pressure is reduced in an incremental manner to a final pressure in the range of 0–4 psia and the temperature of the reaction mixture is increased in an incremental manner to a final temperature not in excess of 275° C. while agitating the reaction mixture, thereby reacting the propoxylated glycerin with the fatty acid to form the fatty acid-esterified propoxylated glycerin and water, and removing the water from the reaction zone (preferably, as an overhead stream), wherein the pressure and temperature are controlled so as to avoid distillative removal of components of the reaction mixture other than water from the reaction zone. The reaction mixture is desirably treated in such manner for a time effective to accomplish at least 90% esterification of the propoxylated glycerin.

DETAILED DESCRIPTION OF THE INVENTION

The propoxylated glycerin reactant employed in the process of this invention may be prepared by any of the standard methods known in the art such as, for example, the base-catalyzed reaction of propylene oxide with glycerin. While the molar ratio of propylene oxide to glycerin is not critical, if the esterified propoxylated glycerin is to be used as a reduced calorie fat substitute it is preferred that from 2 to 20 moles of epoxide be reacted per mole of glycerin. The propoxylation of glycerin can be carried out by the addition of propylene oxide to glycerin in the presence of a catalytic amount of an alkali metal alkoxylate at a temperature of from about 70° C. to 130° C. The alkali metal alkoxylate is desirably prepared by heating an alkali metal compound such as sodium hydroxide or potassium hydroxide with glycerin at an elevated temperature while continuously removing water, preferably under reduced pressure. Preferably, sufficient catalyst is present during propoxylation to provide an alkali metal content of about 0.0003 moles to 3.3 moles alkali metal per 100 g of glycerin. The propylene oxide is preferably fed incrementally into a reactor containing the glycerin and catalyst at a rate sufficient to maintain a pressure within the reactor of about 40 to 80 psia. The degree of propoxylation is controlled, and thus the molecular weight of the propoxylated glycerin as well, by regulating the amount of propylene oxide fed to the reactor. After the desired molecular weight is reached, the alkali metal may be removed prior to esterification by any suitable method such as absorption, ion exchange, or extraction.

The propoxylated glycerin thus obtained will have a chemical structure generally as follows:

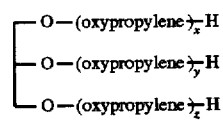

wherein x, y, and z are the same or different and are 0 or preferably an integer of from 1 to 20 with the sum of x+y+z preferably ranging from 2 to 20 (more preferably, 3 to 15). The oxypropylene units in the propoxylated glycerin have the structure

with the former type of structure preferably predominating.

The fatty acids which may be employed as reactants in the present invention may be saturated or unsaturated fatty acids or mixtures thereof. Straight chain as well as branched fatty acids may be used. Preferably, the fatty acid is a $C_{10}$–$C_{24}$ fatty acid (i.e., an acid which contains from 10 to 24 carbon atoms). The fatty acid may be a polycarboxylic acid (for example, a dimer or trimer fatty acid). An excess of fatty acid, preferably from 1 to 40% molar excess relative to the amount of propoxylated glycerin, is employed in the present process in order to catalyze the desired esterification such that the desired esterified propoxylated glycerin product may be rapidly obtained without adding other catalysts. Illustrative of the $C_{10}$–$C_{24}$ fatty acids which may be utilized are saturated acids such as capric, lauric, myristic, pentadecanoic, palmitic, heptadecanoic, stearic, nonadecanoic, eicosanoic, and behenic acid. Unsaturated fatty acids which are suitable for use include palmitoleic, oleic, linoleic, linolenic, and arachidonic acid. The mixtures of fatty acids which are conveniently available by conventional splitting (hydrolysis) of natural and hydrogenated vegetable oils and animal fats are also appropriate for use such as, for example, soybean oil fatty acids, hydrogenated high erucic rapeseed oil fatty acids, coconut oil fatty acids and the like. An important advantage of the present invention is that a large excess of fatty acid need not be used, since minimal fatty acid will be lost from the reactor. The process may thus be advantageously performed with only 5–15% molar excess fatty acid.

The propoxylated glycerin and the fatty acid are introduced into a reaction zone to form a reaction mixture. The component reactants may be added separately or, if so desired, first combined or blended prior to entering the reaction zone. The reaction mixture is initially at a temperature of from about 20° C. to 80° C. and a pressure of from about 13 to 16 psia. The initial pressure, for example, may conveniently be atmospheric pressure and the initial temperature may be room temperature or, if needed to completely melt the reactants to form a homogeneous liquid phase, somewhat higher than room temperature. While the configuration and design of the reaction zone is not critical, a reactor vessel should be selected which is capable of heating and agitating (mixing) the contents of the vessel under subatmospheric pressure. Means for introducing the reactants and for removing the water of reaction (preferably, as an overhead stream in vapor form) from the vessel should also be provided. It may be advantageous to utilize equipment which will provide high shear mixing (e.g., a 5 to 600 m/min. tip speed, which typically may be achieved by a drive motor energy input of 1.5 to 3 kilowatts per 1000 liters of reaction mixture). Thin film reaction systems may also be employed. In a particularly desirable embodiment of the invention, no materials other than the fatty acid and the propoxylated glycerin are introduced into the reaction zone; i.e., no catalyst, solvent, entrainer, or azeotropic stripping agent is present.

The pressure is thereafter reduced in an incremental manner within the reaction zone simultaneous with incrementally increasing the temperature of the reaction mixture. In a preferred embodiment of the invention, the pressure is reduced below atmospheric pressure by the time the temperature of the reaction mixture exceeds 80° C. The reaction mixture is agitated while removing from the reaction zone the water generated by esterification of the propoxylated glycerin by the fatty acid, preferably in vapor form as an overhead stream. Removal of the water has been found to be essential to driving the esterification, which is an equilibrium reaction, to the desired degree of completion. It has been found that esterification may be most rapidly completed if the concentration of water in the reaction mixture is maintained below 5 weight % (more preferably, below 1 weight %) by controlling the rate of water removal. At the same time, the pressure is not lowered and the temperature is not increased at rates such that components of the reaction mixture other than water are removed to any significant extent in vapor or entrained form from the reaction zone. That is, it has been found that if both the temperature and pressure are initially or quickly set to the values which will ultimately be necessary to accomplish complete esterification, the large volume of water which is rapidly evolved causes certain of the more volatile species present in the reaction mixture (such as, for example, unreacted fatty acids, especially shorter chain fatty acids or propoxylated glycerin containing a minimal number of oxypropylene units) to be lost from the reaction zone together with the water. A portion of such losses may be due to the steam stripping effect of the water, while foaming, "bumping", and entrainment phenomena may also contribute to the undesired removal of the reactant components. Put a different way, it is critical to keep a sufficiently low pressure and sufficiently high temperature to quickly remove water but not such a low pressure or high temperature that fatty acids and the like are stripped from the reaction vessel.

The rates at which the pressure and temperature are incrementally adjusted are preferably selected such that the desired level of esterification of the propoxylated glycerin is obtained within a practically short period of time (e.g., 12 hours or less) while minimizing losses of organic substances from the reaction zone. The rates at which pressure and temperature are varied may be constant or may, if so desired, be increased or decreased periodically. In one embodiment of the invention, for example, the rate of temperature increase is fairly high during the first 1–2 hours of the reaction while the rate of pressure decrease is relatively low during such period. The present invention is capable of being operated such that less than 5% (preferably, less than 1%) of the fatty acid which is initially charged to the reaction zone is lost during the course of esterification. Preferably, the molar ratio of water to fatty acid being removed from the reaction zone is at least 10:1. The optimum reaction parameters will vary somewhat depending upon such factors as the amount of excess fatty acid and the relative reactivities and volatilities of the fatty acid and propoxylated glycerin reactants, but may be readily determined by routine experimentation. At the temperatures show below, it will, in one embodiment of the invention, be desirable to maintain the pressure within the following ranges:

| Temp, °C. | Pressure Range, psia |
| --- | --- |
| 100 | 11.5–14.5 |
| 125 | 9.5–14.2 |
| 150 | 7.5–13.8 |
| 175 | 5.5–13.5 |
| 200 | 3.5–12.0 |

Preferably, the pressure is incrementally adjusted so as to be maintained within the following ranges at the times shown (as measured from the time at which pressure decreases are initiated):

| Elapsed Time, hrs. | Pressure Range, psia |
| --- | --- |
| 0.0 | 13–16 |
| 0.5 | 10–14.2 |
| 1.0 | 6–13.5 |
| 1.5 | 4–12 |
| 2.0 | 2–10 |
| 2.5 | 0.7–7.5 |
| 3.0 | 0–5.5 |
| 3.5 | 0–4 |
| to end of esterification | |

Preferably, the temperature is incrementally adjusted so as to be maintained within the following ranges at the times shown (as measured from the time at which temperature increases are initiated):

| Elapsed Time, hrs. | Temperature Range, °C. |
| --- | --- |
| 0.0 | 20–80 |
| 0.5 | 75–125 |
| 1.0 | 125–175 |
| 1.5 | 175–225 |
| 2.0 | 200–260 |
| to end of esterification | |

In one desirable embodiment, the rate of temperature increase is such that a temperature within 20° C. of the final temperature is attained within 1.5 to 4 hours of the time at which the temperature increases are initiated.

The process of the present invention may be performed in a batch, continuous, or semi-continuous manner. When operated in a batch mode, for example, the initial reactants may be simply combined in a single vessel and then subjected to the temperature and pressure regimen described hereinabove such that the entire contents of the vessel are exposed simultaneously to the same reaction conditions. In a continuous process, the fatty acid and propoxylated glycerin may be introduced at one end of a reactor under the initial temperature and pressure conditions set forth above and then carried forward through the reactor in a series of stages or the like wherein the temperature is incrementally increased and the pressure is incrementally lowered in each successive stage, with the esterified propoxylated glycerin product being withdrawn from the other end of the reactor. Means are provided within each stage for withdrawing water vapor from the reaction mixture. A multiple stage continuous stirred tank reactor battery or cascade comprising two or more separate reactors or a multiple stage continuous stirred tank in a single shell may be utilized, for example.

The temperature of the reaction mixture is gradually increased through the course of the process until a final temperature not exceeding 275° C. is attained. In a preferred embodiment, the final temperature does not exceed 260° C. since some degradation of the reactants and/or esterified propoxylated glycerin may take place at higher temperatures. The final temperature is preferably at least 120° C. higher (more preferably, at least 150° C. higher) than the initial temperature. A final pressure of 4 psia or less (i.e., 0–4 psia) has been found to be necessary in order to drive the esterification reaction to a desirably high level of completion in a practically short period of time. Generally, it will be preferred to esterify at least 90% (more preferably, at least 95%) of the available hydroxyl groups of the propoxylated glycerin. To rapidly attain such a high level of esterification, it will also be advantageous for the final temperature to be at least 200° C. The reaction mixture can be maintained at the final temperature and pressure for such time as may be needed to achieve the desired degree of esterification; depending upon the final temperature and pressure selected, this time may vary from as little as 1 minute to as long as 4 to 6 hours or longer. The total time required for esterification, as measured from the time variation of the pressure and temperature is initiated, will typically be from 4 to 15 hours.

Once the desired degree of esterification has been accomplished, any residual unreacted fatty acid should be removed from the esterified propoxylated glycerin so as to lower the acidity to a level which will be acceptable in food applications. Suitable methods include vacuum steam stripping (distillation) at an elevated temperature (as described, for example, in U.S. Pat. No. 4,983,329), alkali neutralization to precipitate fatty acid salts which may then be removed by filtration, extraction (with methanol, for example), and dilution with a solvent such as hexane in which the desired product is soluble and the fatty acid is insoluble and the precipitated fatty acid removed by filtration.

The esterified propoxylated glycerin produced by the process of this invention can be additionally purified or treated so as to render it more suitable for use in food compositions using any of the techniques known in the art for refining natural vegetable or animal oils and fats. Such techniques include, but are not limited to, degumming, bleaching, filtration, deodorization, hydrogenation, dewaxing, and the like. Various additives such as stabilizers, anti-oxidants, vitamins and so forth can also be incorporated into the esterified propoxylated glycerin.

EXAMPLES 1–3

A reactor was charged with varying amounts of Emery 610 soya fatty acids (a mixture of fatty acids derived from soybean oil) and propoxylated glycerin (glycerin reacted with 8 equivalents of propylene oxide; molecular weight ca. 550) at ambient temperature and pressure. The amounts of the reactants used are listed in Table 1. The temperature of the reactor contents was incrementally increased to 240° C. and the pressure within the reactor incrementally decreased to a value of 1.5 psi or less in accordance with Table 2. Each example was held at 240° C. and approximately the lowest pressure shown in Table 2 until about 95% conversion of the hydroxyl groups in the propoxylated glycerin was achieved. The total reaction times were as follows: Example 1, 15 hours; Example 7, 9.5–11.5 hours; Example 3, 11.5 hours.

TABLE 1

|  | Example No. | | |
| --- | --- | --- | --- |
|  | 1 | 2 | 3 |
| Fatty Acid, Kg | 16.13 | 17.67 | 16.82 |
| Propoxylated Glycerin, Kg | 8.06 | 8.26 | 7.86 |
| % Excess Fatty Acid | 30 | 40 | 40 |

TABLE 2

| | | Example No. | | |
| --- | --- | --- | --- | --- |
| | | 1 | 2 | 3 |
| Time, hrs. | Temp., °C. | | Press., psia | |
| 0.0 | 25 | 14.7 | 14.7 | 14.7 |
| 1.5 | 200 | 13.9 | 14.0 | |
| 2.0 | 240 | | | 7.5 |
| 2.5 | 240 | 6.0 | 4.3 | |
| 3.5 | 240 | 5.7 | 1.5 | |
| 5.5 | 240 | 1.0 | | 5.4 |
| 6.5 | 240 | | | 3.4 |
| 7.5 | 240 | | | 2.0 |
| 8.5 | 240 | | | 1.2 |

EXAMPLE 4

The procedure of Examples 1–3 was repeated, except that a 5% molar excess of fatty acid relative to propoxylated glycerin and a propoxylated glycerin containing an average of 5 oxypropylene units per equivalent of glycerin were used. The pressure and temperature were varied over the course of the reaction as indicated in Table 3. Conversion of 90% of the hydroxy groups in the propoxylated glycerin was achieved after 11 hours.

TABLE 3

| Time, hrs. | Temp, °C. | Pressure, psia | Conversion, % |
| --- | --- | --- | --- |
| 0 | 60 | 14.7 | ca. 0 |
| 0.5 | 100 | 13.0 | |
| 1.0 | 150 | 10.6 | |
| 1.25 | | | 35 |
| 1.50 | 200 | 8.0 | |
| 2.0 | 240 | 6.0 | |
| 2.25 | 240 | | 37 |
| 2.5 | 240 | 4.4 | 62 |
| 3.0 | 240 | 2.6 | |
| 3.5 | 240 | 1.5 | |
| 4.0 | 240 | 0.5 | |
| 4.5 | 240 | ca. 0.25 | 73 |
| 5.5 | 240 | ca. 0.25 | 75 |
| 6.5 | 240 | ca. 0.25 | 81 |
| 7.5 | 240 | ca. 0.25 | 87 |
| 8.5 | 240 | ca. 0.25 | 87 |
| 9.25 | 240 | ca. 0.25 | 88 |
| 11 | 240 | ca. 0.25 | 90 |

EXAMPLE 5

The procedure of Example 4 was repeated, except that the pressure within the reactor was decreased more rapidly as indicated in the following Table 4. Conversion of >95% of the hydroxy groups in the propoxylated glycerin was achieved after only 7 hours.

TABLE 4

| Time, hrs. | Temp., °C. | Pressure, psia | Conversion, % |
| --- | --- | --- | --- |
| 0 | 60 | 14.7 | 0 |
| 0.5 | 100 | 12.0 | |
| 1.0 | 150 | 8.0 | 5 |
| 1.5 | 200 | 5.6 | |
| 2.0 | 240 | 4.0 | 37 |
| 2.5 | 240 | 2.4 | |
| 3.0 | 240 | 1.3 | 74 |
| 3.5 | 240 | 0.5 | |
| 4.0 | 240 | ca. 0.25 | 86 |
| 5.0 | 240 | ca. 0.25 | 92 |
| 6.0 | 240 | ca. 0.25 | 92 |
| 7.0 | 240 | ca. 0.25 | 96 |

I claim:

1. A process for producing a fatty acid-esterified propoxylated glycerin comprising the steps of
   (a) introducing a propoxylated glycerin and a molar excess of fatty acid into a reaction zone to form a reaction mixture;
   (b) beginning at an initial temperature of from about 20° C. to 80° C. and an initial pressure of from about 13 to 16 psia, simultaneously reducing the pressure in an incremental manner to a final pressure of 4 psia or less and increasing the temperature of the reaction mixture in an incremental manner to a final temperature of at least 200° C. but not in excess of 275° C. while agitating the reaction mixture and removing the water generated by esterification of the propoxylated glycerin with the fatty acid from the reaction zone as an overhead stream, wherein the pressure and temperature are adjusted so as to avoid distillative removal of components of the reaction mixture other than water from the reaction zone, for a time effective to accomplish at least 90% esterification of the propoxylated glycerin.

2. The process of claim 1 wherein the propoxylated glycerin comprises from 2 to 20 oxypropylene units per equivalent of glycerin.

3. The process of claim 1 wherein the molar excess of fatty acid is from 1% to 40% relative to propoxylated glycerin.

4. The process of claim 1 wherein step (b) is accomplished within a period of from 4 to 15 hours.

5. The process of claim 1 wherein the fatty acid is selected from $C_{10}$–$C_{24}$ fatty acids and mixtures thereof.

6. The process of claim 1 wherein said process is performed in the absence of any catalyst other than the excess fatty acid.

7. The process of claim 1 wherein at least 95% esterification of the propoxylated glycerin is accomplished.

8. The process of claim 1 wherein when the temperature during step (b) has value T, the pressure is within the range P as follows:

| T (°C.) | P (psia) |
| --- | --- |
| 100 | 11.5–14.5 |
| 125 | 9.5–14.2 |
| 150 | 7.5–13.8 |
| 175 | 5.5–13.5 |
| 200 | 3.5–12.0 |

9. The process of claim 1 wherein the pressure is reduced below atmospheric pressure by the time the temperature of the reaction mixture exceeds 80° C.

10. The process of claim 1 wherein said process is performed in a batch manner.

11. The process of claim 1 wherein said process is performed in a continuous manner.

12. The process of claim 1 wherein said process is performed using a multiple stage continuous stirred tank reactor battery.

13. The process of claim 1 wherein said process is performed using a multiple stage continuous stirred tank in a single shell.

14. A process for producing a fatty acid-esterified propoxylated glycerin comprising the steps of (a) introducing a propoxylated glycerin comprising from 2 to 20 oxypropylene units per equivalent of glycerin and a 1 to 40% molar excess of a fatty acid selected from $C_{10}$–$C_{24}$ fatty acids and mixtures thereof into a reaction zone to form a reaction mixture;

(b) beginning at an initial temperature of from about 20° C. to 80° C. and an initial pressure of from about 13 to 16 psia, simultaneously reducing the pressure in an incremental manner to a final pressure of 4 psia or less and increasing the temperature of the reaction mixture in an incremental manner to a final temperature of from 200° C. to 260° C. while agitating the reaction mixture and removing the water generated by esterification of the propoxylated glycerin with the fatty acid from the reaction zone as an overhead stream, wherein the pressure and temperature are adjusted so as to avoid distillative removal of components of the reaction mixture other than water from the reaction zone and the pressure is reduced below atmospheric pressure by the time the temperature exceeds 80° C., for a time effective to accomplish at least 95% esterification of the propoxylated glycerin.

15. The process of claim 14 wherein the temperature and pressure are maintained within the following ranges:

| Elapsed time, hrs. | Pressure, psia | Temperature, °C. |
|---|---|---|
| 0.5 | 10–14.2 | 75–125 |
| 1.0 | 6–13.5 | 125–175 |
| 1.5 | 4–12 | 175–225 |
| 2.0 | 2–10 | 200–260 |
| 2.5 | 0.7–7.5 | 200–260 |
| 3.0 | 0–5.5 | 200–260 |
| 3.5 and thereafter | 0–4 | 200–260 | wherein elapsed time is measured from the time at which the temperature increases and pressure decreases are initiated in step (b).

* * * * *